United States Statutory Invention Registration [19]

[11] Reg. Number: H516

Lattin et al. [43] Published: Sep. 6, 1988

[54] IONTOPHORTETIC DEVICE

[75] Inventors: Gary A. Lattin, Forest Lake; Richard Spevak, Minneapolis, both of Minn.

[73] Assignee: Medtronic, Inc., Minneapolis, Minn.

[21] Appl. No.: 240,740

[22] Filed: Mar. 5, 1981

[51] Int. Cl.[4] ..... A61N 1/30
[52] U.S. Cl. ..... 604/20; 128/802
[58] Field of Search ..... 128/207.21, 498, 802, 128/803, 640, 641; 604/20

[56] References Cited

U.S. PATENT DOCUMENTS

| | | | |
|---|---|---|---|
| 568,095 | 9/1896 | Muir . | |
| 2,590,876 | 4/1952 | Landaver | 128/802 X |
| 2,784,715 | 3/1957 | Kestler | 128/207.21 |
| 3,025,858 | 3/1962 | Browner | 128/422 |
| 3,122,137 | 2/1964 | Erlanger | 128/172.1 |
| 3,163,166 | 12/1964 | Brant et al. | 128/405 |
| 3,215,139 | 11/1965 | Dietz | 128/172.1 |
| 3,315,665 | 4/1967 | MacLeod | 128/24.5 |
| 3,472,233 | 10/1969 | Sarbacher | 128/422 |
| 3,699,963 | 10/1972 | Zaffaroni | 128/268 |
| 3,716,054 | 2/1973 | Porter et al. | 128/172.1 |
| 3,794,910 | 2/1974 | Ninke et al. | 324/30 R |
| 3,955,583 | 5/1976 | Horauf | 128/420 R |
| 3,964,477 | 6/1976 | Ellis et al. | 128/172.1 |
| 3,989,050 | 11/1976 | Buchalter | 128/419 R |
| 4,002,221 | 1/1977 | Buchalter | 181/0.5 |
| 4,019,510 | 4/1977 | Ellis | 128/172.1 |
| 4,051,842 | 10/1977 | Hazel et al. | 128/2.06 E |
| 4,066,078 | 1/1978 | Berg | 128/2.06 E |
| 4,082,087 | 4/1978 | Howson | 128/640 |
| 4,094,822 | 6/1978 | Kater | 252/512 |
| 4,125,110 | 11/1978 | Hymes | 128/641 |
| 4,141,359 | 2/1979 | Jacobsen et al. | 128/207.21 |
| 4,177,817 | 12/1979 | Bevilacqua | 128/803 |
| 4,209,020 | 6/1980 | Nielsen | 128/640 |
| 4,211,222 | 7/1980 | Tapper | 128/207.21 |

List continued on next page.

FOREIGN PATENT DOCUMENTS

| | | | |
|---|---|---|---|
| 1965195 | 7/1971 | Fed. Rep. of Germany | 128/640 |
| 2147704 | 11/1972 | Fed. Rep. of Germany . | |
| 2558525 | 8/1976 | Fed. Rep. of Germany . | |
| 2724461 | 12/1977 | Fed. Rep. of Germany . | |
| 2740270 | 3/1979 | Fed. Rep. of Germany . | |
| 2307554 | 4/1975 | France . | |
| 2336144 | 12/1975 | France . | |
| 2351670 | 1/1978 | France | 128/207.21 |
| 424006 | 11/1966 | Switzerland . | |
| 410009 | 5/1934 | United Kingdom . | |
| 2030453 | 4/1980 | United Kingdom . | |
| 2045088 | 10/1980 | United Kingdom | 128/640 |
| 706092 | 11/1979 | U.S.S.R. . | |

OTHER PUBLICATIONS

"Painless Anesthesia" by Yvonne Baskin in Medical Electronics, Sep. 1979, pp. 60 and 61.

List continued on next page.

*Primary Examiner*—Charles T. Jordan
*Assistant Examiner*—Michael J. Carone
*Attorney, Agent, or Firm*—Reed A. Duthler; John L. Rooney; Joseph F. Breimayer

[57] ABSTRACT

An improved iontophoretic device for introducing an ionic substance into body tissue. A compact casing contains all the electronic circuitry necessary for generation and control of an iontrophoretic current. Stainless steel electrode plates are mounted directly on the casing and are electrically coupled to the electronics within. The device may be used in a simplified iontophoretic procedure: adhesive pads containing the ionic substance to be driven into the body tissue are applied to the stainless steel plates and the entire iontophoretic device is then affixed to the body by the adhesive pads and a safety strap, thus permitting normal patient movement during the iontophoretic process.

6 Claims, 2 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

U.S. PATENT DOCUMENTS

| | | | |
|---|---|---|---|
| 4,230,105 | 10/1980 | Harwood | 128/156 |
| 4,239,046 | 12/1980 | Ong | 128/640 |
| 4,248,247 | 2/1981 | Ware | 128/798 |
| 4,250,878 | 2/1981 | Jacobsen et al. | 128/207.21 |
| 4,257,424 | 3/1981 | Cartmell | 128/641 |
| 4,273,135 | 6/1981 | Larimore et al. | 128/640 |
| 4,274,420 | 6/1981 | Hymes | 128/641 |
| 4,307,717 | 12/1981 | Hymes et al. | 128/156 |
| 4,317,457 | 3/1982 | Guillot | 128/783 |
| 4,325,367 | 4/1982 | Tapper | 128/803 X |
| 4,352,359 | 10/1982 | Larimore et al. | 128/640 |
| 4,381,012 | 4/1983 | Russek | 128/644 |
| 4,383,529 | 5/1983 | Webster | 128/802 X |
| 4,391,278 | 7/1983 | Cahalan et al. | 128/640 |
| 4,416,274 | 11/1983 | Jacobsen et al. | 604/20 |

OTHER PUBLICATIONS

"Iontophoretic Local Anesthesia for Conjunctional Surgery" by Hampson A. Sisler, M.D. in Annals of Opthalmology, vol. 10, 1978, pp. 597 and 598.

"Iontophoresis—A Major Advancement, Editorial in the Eye, Ear, Nose and Throat Monthly, vol. 55, Feb. 1976, pp. 13 and 14.

"Treatment of Orthopaedic Infections with Electrically Generated Silver Ions" by Robert O. Becker and Joseph A. Spadaro, in the Journal of Bone and Joint Surgery (American Volume), vol. 60-A, No. 7, Oct. 1978, pp. 871-881.

"Techniques for Iontophoresis" Letter by Charles M. Magistro and response by Joseph Kahn in Physical Therapy, vol. 57, No. 10, Oct. 1977, pp. 1193 and 1194.

"Iontophoresis—The Non-Invasive Administration of Drugs", Sales brochure of Motion Control, Inc., 1005 South 300 West, Salt Lake City, Utah 84101, Form No. MCl 009-2/79.

"Phoresor—Iontophoretic Drug Delivery System—Instructions", Instruction Sheet distributed by Motion Control, Inc., 1005 South 300 West, Salt Lake City, Utah 84101, Form No. MC10017-6/79.

"Acetic Acid Iontophoresis for Calcium Deposits by Joseph Kahn in Physical Therapy, vol. 57, No. 6, Jun. 1977, pp. 658 and 659.

1978 Corporate Report of ALZA Corporation, pp. 1-11, available from ALZA Corp., 3170 Porter Dr., Palo Alto, Calif. 94304.

Sales brochure distributed by Medco Products, Inc., 3601 East Admiral Place, Tulsa, Oklahoma 74115, Form No. HV 103673, Jun. 1979, 5 pages.

"Iontophoresis"-An excerpt from an article in the Journal of the New York State Society of Physiotherapists, Inc., Annual Issue, Jun., 1959, by Arthur Kahn and Joseph Kahn with updated material (received from Medco Products Co., Inc.).

"D.C. (Galvanic) Current"-Information Sheet distributed by Medco Products Co., Inc., 3601 East Admiral Place, Tulsa, Oklahoma 74115.

"Electro-Diagnosis"-Information Sheet No. 6301152, Distributed by Medco Products Co., Inc., 3601 East Admiral Place, Tulsa, OK 74115.

IONTOPHORTETIC DEVICE

CROSS-REFERENCE TO CO-PENDING APPLICATION

Reference is made to commonly assigned U.S. application Ser. No. 241,150 by Spevak, Lattin and Jevne for an Iontophoretic Electrode, which discloses electrodes suitable for use with the iontophoresis device claimed below.

BACKGROUND OF THE INVENTION

1. Field of the Invention

This invention in general relates to the field of iontophopretic introduction of ionic substances into a body, and more particularly concerns an improved device which simplifies the iontophoretic administration of ionic substances, and permits a patient to be normally ambulatory during the administration of the substance.

2. Description of the Prior Art

Iontophoresis is a method for introducing ionic substances into a body. The method utilizes direct electrical current to drive the ionized substances, such as chemicals or drugs, through the intact skin or other body surface. This has proven to be very useful in numerous medical applications. See U.S. Pat. Nos. 3,991,755 issued to Jack A. Vernon, et al, 4,141,359 issued to Stephen C. Jacobson et al. Prior art iontophoretic devices generally comprise an iontophoretic current generator and a pair of electrodes. The electrode containing the ionic substance to be introduced into the body is generally known as the active electrode while the other electrode is called the ground or indifferent electrode. The current generator is generally a hand-held or table-supported instrument and the electrodes are connected to the generator by means of wires. The electrodes, especially the active electrodes, generally are relatively complex devices, including a cup or other receptacle for holding a fluid solution of the ionic substance in contact with the body, a means for making electrical contact with the solution, and a means for holding the electrode firmly to the body. Such electronic devices also require the use of some means for introducing the solution containing the ionic substance into the electrode receptacle, such as a syringe. Relatively high skill levels are thus required for the use of the prior art iontophoretic devices (compared for example to the skill required to apply a bandage). These devices also require the patient to remain in a fixed location during iontophoretic processes, which is a decided disadvantage since the process generally takes time on the order of minutes or sometimes, hours.

U.S. Pat. No. 4,141,359 discloses a compact iontophoretic device in the embodiment shown in FIG. 2 and discussed in Example I of that patent. In this device the grounding electrode is mounted on the current generator housing and tne indifferent electrode is connected to the housing by a wire. This device may be entirely mounted on the body of the patient and thus, presumably some motion of the patient is possible while the device is in use. However, the use of this device still requires a relatively high level of skill and care since the electrodes are of the fluid gel-type. In addition, the gel-type electrodes are subject to some movement on the skin, and the wire can be snagged during movement. Thus, this device does not readily lend itself to ambulatory type applications, especially in the case of young children who tend to have highly mobile limbs.

SUMMARY OF THE INVENTION

The invention provides a device for use in iontophoretically introducing an ionic substance into body tissue comprising a casing containing an electric current source, a first electrode plate means mounted on the casing for receiving a first electrode element and for electrically coupling the first electrode element to the current source, and a second electrode means mounted on the case and coupled to the current source. Preferably the second electrode means is also a plate means for receiving a second electrode element. Preferably the plates are composed of stainless steel. The casing and plate combination forms an integral unit that can survive considerable abuse and requires little care. The device may be utlized by applying adhesive electrode pads to the metal plates and then applying the entire unit to the body in a manner similar to the application of a self-adhesive bandage. Thus this iontophoretic device lends itself to rapid use and reuse that, for the first time, makes iontophoretic devices available for ambulatory therapeutic and diagnostic uses.

A safety strap may be fixed to the casing for further securing the device to the body; the safety strap is particularly useful when the electronics of the current source are relatively bulky, but as the electronics are reduced, as for example when custom microelectronic circuits and power sources are used, the safety strap may be eliminated.

Numerous other features, objects and advantages of the invention will become apparent from the following detailed description when read in conjunction with the accompanying drawing.

DESCRIPTION OF THE PREFERRED EMBODIMENT

Figure 1:
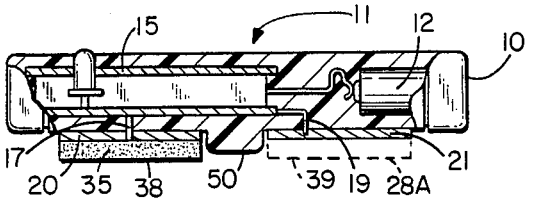
FIG. 1 is a partially cut away side view of a preferred embodiment of an iontophoretic device according to the invention showing one adhesive electrode pad in place on the device.

A cut away view of an exemplary embodiment of the invention is shown in FIG. 1. Casing 10 contains electric current source 11 which includes a battery power source 12 and an electronics package 15. The electric current source 11 is coupled via leads 17 and 19 to electrode plate means 20 and 21 respectively.

Figure 2A:
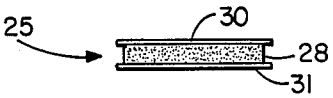
FIG. 2*a* is an end view of an adhesive electrode as it may be manufactured and sold.
Figure 2B:
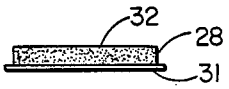
FIG. 2*b* shows the electrode pad of FIG. 2*a* just prior to its application to a preferred embodiment of the invention.

The embodiment of the invention shown in FIG. 1 may be prepared for use by applying electrode elements, such as shown in FIGS. 2*a* and 2*b* to electrode plates 20 and 21. The electrode 25 comprises a sheet-like adhesive pad 28 having protective backing sheets 30 and 31 covering its broad surfaces as shown in FIG. 2*a*. In FIG. 2*b* the protective sheet 30 has been removed exposing the adhesive surface 32. The pad 28 may be then applied to one of the electrode plates of the device such as 21. In FIG. 1 the pad is shown in ghost at 28*a* in the position it would occupy when applied to plate 21. The entire device may then be applied to the body. It is understood that "body" is used in its most general sense and includes plant, animal and human bodies.

Adhesive pads such as 35 and 28 are composed of an ionic substance admixed with an adhesive. When the device of FIG. 1 is applied on the body with the lower surfaces such as 38 of the pads against the body and the device is turned on, the ionic substance in one or both of the pads is driven into the body. For example, if the ionic substance that is desired to drive into the body is a positive ionic substance, a pad containing this substance may be placed on the positive electrode plate 20 and an indifferent electrode pad in which the ionic substance may be a salt such as sodium chloride, which has ions of both positive and negative polarity, may be placed on the negative electrode. The electrode pads such as 28 and 35 and the backing sheets, such as 30 and 31, may be color-coded for identification and/or may be marked with positive or negative symbols to clearly identify which of plates 20 and 21 they should be applied to. The adhesive pads such as 28 and 35 are more fully discussed in U.S. patent application Ser. No. 241,150 now abandoned, a companion application to the present application.

Figure 3:
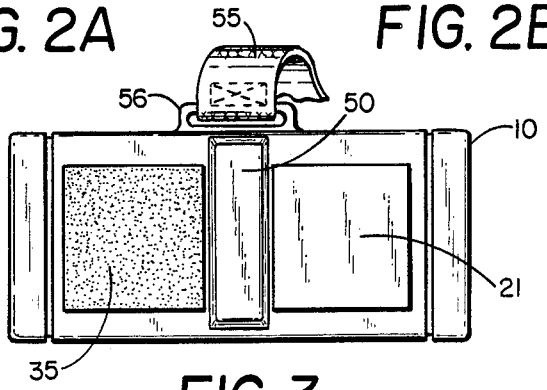
FIG. 3 is a bottom view of the device of FIG. 1.

Turning attention to FIG. 3 a bottom view of the device according to the invention is shown. It is seen that in this embodiment the plates 20 (shown covered with pad 35 in FIG. 3) and 21 are of generally square shape, although any shape may be chosen. The negative sign on plate 21 is shown. A positive sign on plate 20 is covered by pad 35. Plates 20 and 21 are separated by a raised ridge 50, portion of housing 10, which ridge 50 ensures the electrical separation of pads 35 and 28*a*. As can be seen in FIG. 1, ridge 50 extends below the surface of plates 20 and 21 but does not extend as far as the surfaces 38 and 39 of pads 35 and 28*a*. Should the iontophoretic device be attached to the limb or other portion of the body with such force that pads 35 and 28 become compressed, or if pads 35 and 28*a* should become displaced in a horizontal direction from their correct position, ridge 50 prevents their physical contact which would short out the iontophoretic circuit. Ridge 50 also assists in the rapid application of pads such as 35 and 28A to plates 20 and 21.

Strap 55 is provided to assist in holding device 11 to the body to which the device is applied. Strap 55 is attached to strap anchor 56 on housing 10. In the embodiment shown, strap 55 is a material which adheres to itself, such as VELCRO TM. It attaches to itself after circling the limb or other body portion, and thus only one strap anchor 56 is necessary. Strap 55 is provided because in the embodiment shown, housing 10, battery 12 and electronics 15 have sufficient mass so that the device might become separated from the body during rapid movements of the limb or other body portion to which it is applied. The invention contemplates that circuitry 15 and power source 12 may be made extremely small and of relatively low mass using state of the art technology, in which case strap 55 may be eliminated.

Figure 4:
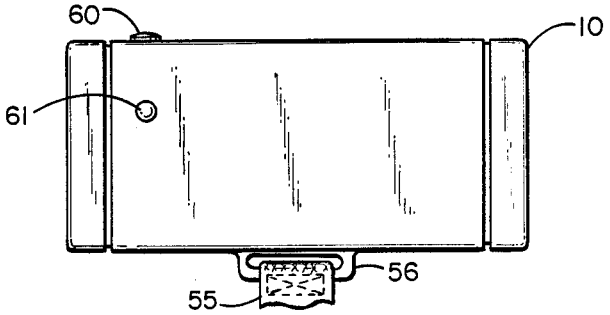
FIG. 4 is a top view of the device of FIG. 1.

As shown in FIG. 4, OFF/ON switch 60 and light-emitting diode (L.E.D.) 61 protrude through housing 10. Switch 60 is used to activate the iontophoretic device. Diode 61 serves to indicate whether the current is on or off and provides battery life indication. These shall be discussed below in more detail in connection with the electronic circuitry.

Figure 5:
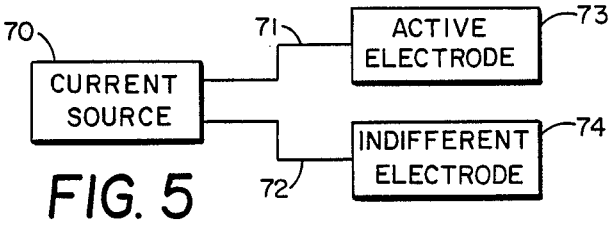
FIG. 5 is a block diagramatic illustration of circuitry for an iontophoretic device.

Turning to FIG. 5 there is shown a block diagrammatic illustration of the iontophoretic circuit. This circuit includes current source 70 which is electrically coupled through coupling means 71 and 72 to electrodes 73 and 74. For purposes of illustration, electrode 73 is labeled the active electrode while electrode 74 is labeled the indifferent electrode, although the positions could be reversed. Coupling means 71 and 72 may be wires or any other means for electrically coupling the current source and the electrodes.

Figure 6:
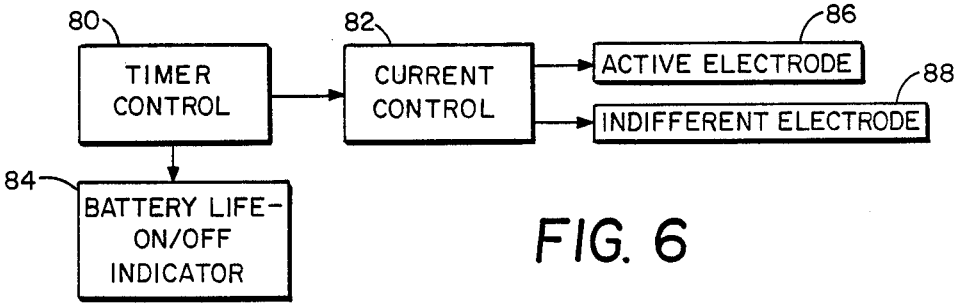
FIG. 6 is a block diagramatic illustration of the preferred electronic circuitry for producing the iontophoretic current.

FIG. 6 shows a more detailed block diagrammatic illustration of the electrical circuit employed in the embodiment of the invention disclosed in reference to FIGS. 1–4. Turning the switch 60 (not shown in FIG. 6) on activates Timer Control Circuit 80. Timer Control Circuit 80 provides a signal to Battery Life-ON/OFF Indicator Circuit 84 which, in turn, activates light-emitting diode 61 provided that the battery voltage is above a predetermined level which is considered to be sufficient to reliably operate the device. Timer Control Circuit 80 also provides a signal to Current Control Circuit 82. Current Control Circuit 82 responds to a signal from Timer Control Circuit 80 to ramp/on the iontophoretic current; that is, the iontophoretic current is turned on gradually from 0 value up to the full current value. This prevents burning, shocking or other unpleasant sensations when the current is turned on. The iontophoretic current is applied from Current Control Circuit 82 to electrodes 86 and 88. In the embodiment shown the current is such that it flows from active electrode 86 through the body to indifferent electrode 88; in other embodiments the electrodes or the direction of the current may be reversed.

The dosage of ionic substance which is applied to the body is controlled by Timer Control Circuit 80 and Current Control Circuit 82. Current Control Circuit 82 provides a constant current output to the electrode which is, within impedance range and as limited by supply voltage, independent of the load between electrodes 86 and 88, which is generally the skin impedance. Thus, the amount of ionic substance driven into the body by the current will be constant in time. In this manner control of the time over which the current is applied controls the dosage. After a predetermined amount of time Timer Control Circuit 80 applies a second signal to Current Control Circuit 82 which causes Current Control Circuit 82 to turn the iontophoretic current off. At the same time a second signal is passed through Battery Life-ON/OFF Indicator Circuit 84 which causes the circuit to turn L.E.D. 61 off.

Figure 7:
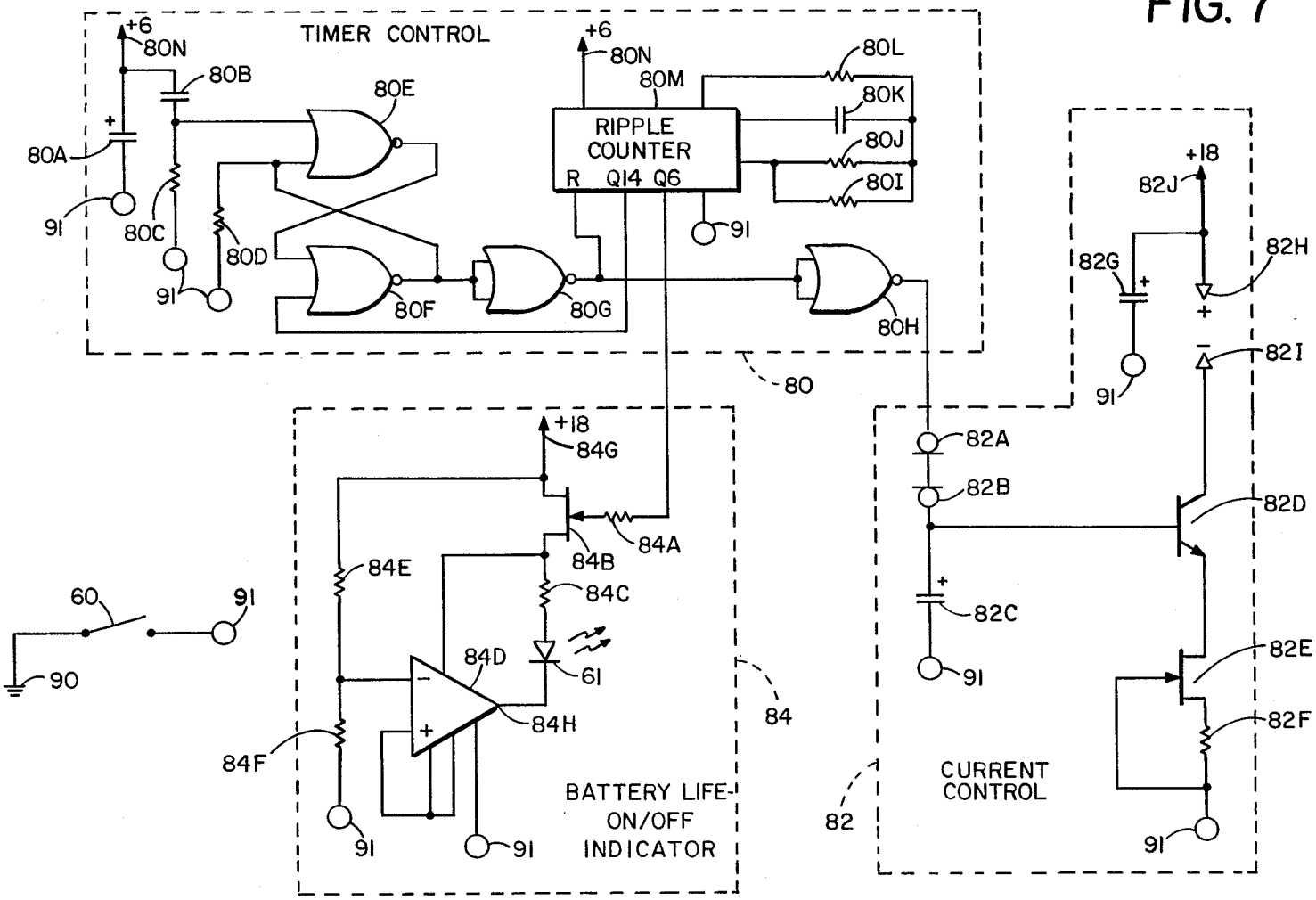
FIG. 7 is a a more detailed diagramatic illustration of the electronic circuitry of FIG. 6.

The electronics for the circuit of FIG. 6 is shown in detail in FIG. 7. Switch 60 connects ground 90 and an input line 91 connecting to each of the subcircuits.

Timer Control Circuit 80 comprises 0.1 microfarad capacitor 80B 1 megohm resistor 80C and 80D, NOR gates 80E through 80H, 910 kilohm resistor 80I, 560 kilohm resistor 80J, 0.056 microfarad capacitor 80K, 3.3 megohm resistor 80L, and ripple counter 80M.

As is well known in the literature, a NOR gate is an electronic device with one output and two or more inputs. If either of the inputs to a NOR gate is the positive circuit voltage (6 volts in the case of the present circuit), referred to as the logic "1" state, then the output of the NOR gate is the ground voltage conventionally referred to as the logic "0" voltage. If all the inputs are in the logic "0" state, then the signal at the output is a logic "1" state. The conventional provisions of power supply voltages and ground voltages to the NOR gates are not shown.

Capacitor 80A is connected between switch 60 and the positive 6 volt voltage terminal 80N. Capacitor 80A is a 33 microfarad filter capacitor whose purpose is to reduce circuit noise. Capacitor 80B is connected between the high voltage side of capacitor 80A and the upper input terminal to NOR gate 80E, which terminal is also connnected to switch 60 through resistor 80C. NOR gates 80E and 80F are cross-coupled in a standard configuration for a flip-flop circuit. The output of NOR gate 80E is connected to the upper input to NOR gate 80F. The lower input to gate 80F is connected to the Q14 counter (No. 3 pin) output of ripple counter 80M, the output of NOR gate 80F is connected to the two inputs of gate 80G and to the lower input of gate 80E, the latter input also being connected to switch 60 through resistor 80D. The output of NOR gate 80G is connected to the RESET input (No. 12 pin) of the ripple counter 80M and also to both inputs of NOR gate 80H. Resistors 80I and 80J are connected in parallel between the No. 10 pin of ripple counter 80M and one side of capacitor 80K, which is also connected through resistor 80L to the No. 11 pin of ripple counter 80M. The other side of capacitor 80K is connected to the No. 9 pin of ripple counter 80M. The No. 8 pin of ripple counter 80M is connected to ground through switch 60 while the No. 16 pin is connected to the +6 volt supply 80N. Ripple counter 80M is a CD 4060 counter divider available from RCA Solid State Division, Box 3200, Somerville, N.J., 08876. The output of NOR gate 80H is applied to the Current Control Circuit which will be described below.

When switch 60 is closed the inputs to NOR gate 80G will be at a logic "0" since they are connected to ground through resistor 80D, and no current is initially flowing in the line. The output of gate 80G will thus be a logic "1" which resets ripple counter 80M setting the Q14 output to a logic "0", and thus the lower input to gate 80F to a logic "0". At the same time, a current will begin flowing in the circuit from positive terminal 80N through resistor 80C to ground (charge will be building on capacitor 80B) which will set the upper input terminal to NOR gate 80E at a logic "1". The output of gate 80E is thus forced to a logic "0" which is applied to the upper input of gate 80F. The two inputs to gate 80F being a logic "0" the output will switch to a logic "1". This causes output of gate 80G to go to a logic "0", which releases the RESET on ripple counter 80M which permits it to begin counting and at the same time causes the output of gate 80H to switch from a logic "0" to a logic "1". While ripple counter 80M is counting upper input to NOR gate 80E falls to a logic "0", however the output of the gate is maintained at a logic "0" because the lower input to the gate is held at a logic "1" as long as the lower input of gate 80F is held to log "0".

Ripple counter 80M is driven by an oscillator circuit consisting of resistors 80I, 80J, 80L and capacitor 80K. The value of resistor 80I is selected so that the oscillation period is 36.6 milliseconds. The ripple counter will count the 36.6 millisecond oscillations so that within approximately 5 minutes, its 14th counter is triggered and the Q14 pin goes to a logic "1". This logic "1" signal applied to the lower input of gate 80F causes output of the gate to go to logic "0", which in turn forces the output of gate 80G to a logic "1" which holds ripple counter 80M RESET and changes the output of NOR gate 80H to a logic "0". The logic "0" output of NOR gate 80F is also applied to the lower input of NOR gate 80E. Both inputs of NOR gate 80E being a logic "0", the output will become a logic "1", which is applied to upper input of NOR gate 80F forming its input to a logic "1", thereby latching gates 80E and 80F in a state such that the output of NOR gate 80H remains a logic "0" until switch 60 is turned off and then on again to restart the cycle. Thus, Timer Control Circuit 80 produces a logic "1" signal to Current Control Circuit 82 for a five-minute period after switch 60 is turned on. While counter 80M is counting up to five minutes, its 6th counter stage will go to a logic "1" approximately every 2.3 seconds. The output of the 6th counter stage (No. 4 pin) will thus go to a logic "1" for a 1.15 second period every 2.3 seconds. This signal is passed to the Battery Life-ON/OFF Indicator Circuit 84 and used as discussed below.

Current Control Circuit 82 includes two constant current 1N 5290 diodes 82A and 82B, 330 microfarad capacitor 82C, a 2N 2222 transistor 82D, a 2N 4341 FET 82E, 510 kilohm resistor 82F, 33 microfarad capacitor 82G and electrodes outputs 82H and 82I.

The anode of constant current diode 82A is connected to the output of NOR gate 80H in Timer Control Circuit 80. The cathode of diode 82A is connected to the cathode of diode 82B while the anode of diode 82B is connected to one side of capacitor 82C and also to the base of transistor 82D. The other side of capacitor 82C is connected to ground through switch 60. The emitter of transistor 82D is connected to the drain of FET 82E. The gate of FET 82E is connected to switch 60 and is also connected to its own source through resistor 82F. The collector of transistor 82D is connected to the negative electrode output 82I which may be connected to plate 21 in the embodiment of the invention shown in FIGS. 1, 3 and 4. The other electrode output 82H, which may be connected to plate 20 in the embodiment shown in FIGS. 1, 3 and 4, is connected to the positive 18 volt power source 82J, and the line between electrode 82H and power source 82J is connected to one side of capacitor 82G. The other side of capacitor 82G is connected to switch 60.

Capacitor 82G is a filter capacitor to eliminate noise in the circuit. When Timer Control Circuit 80 causes NOR gate 80H to go to a logic "1" state immediately after switch 60 is turned on, a 6 volt signal is applied to the anode of diode 82A. Since this is a constant current diode the current that passes through it is fixed and thus the charge on capacitor 82C is built up slowly, over a period of about 1 second. Thus, the voltage applied to the base of transistor 82A builds up slowly, to the full 6 volt value over the same period, causing the transistor to turn on slowly over the same period. FET 82E and resistor 82F form a conventional current-limiting circuit. Resistor 82F is chosen to limit the current to 2 milliamps. A circuit is completed through the body and through electrode output 82H to the positive voltage source. Thus, upon application of the signal from the Timer Control Circuit 80, the Current Control Circuit 82 slowly, over a period of about a second, ramps up the current through the electrode outputs 82I and 82H from 0 to a maximum constant current of 2 milliamps. When, at the end of the 5-minute period, the signal from Timer Control Circuit 80 drops to a logic "0" the charge on capacitor 82C will slowly drain through current-limiting diode 82B, again over about a 1-second period. Thus, the transistor 82D will be slowly turned off over the same period and the current through the electrodes will slowly ramp down to a 0 value.

Battery Life-ON/OFF Indicator Circuit 84 comprises 100 kilohm resistor 84A, 2N4338 FET 84B, 1.5 kilohm resistor 84C, L.E.D. 61, an LN10H differential amplifier 84D, which is available from National Semiconductor Corp. at 2900 Semiconductor Drive, Santa Clara, CA 95051, 820 kilohm resistor 84E and 12 kilohm resistor 84F. The gate of FET 84B is connected to the Q6 output (No. 4 pin) of decade counter 80M in Timer Control Circuit 80 through resistor 84A. The drain of FET 84B is connected to the positive 18 volt power source 84G and to switch 60 through resistor 84E and 84F. The source of FET 84B is connected to the output 84H (No. 6 pin) of amplifier 84D through resistor 84C and L.E.D. 61, and is also connected to the No. 7 pin of amplifier 84D. The negative input terminal (No. 2 pin) of amplifier 84D is connected to the line between resistors 84F and 84E. The positive input terminal (pin No. 3) of amplifier 84D is connected to both the No. 1 and No. 8 pins of the same amplifier. The No. 4 input pin of the amplifier 84E is connected to switch 60.

As discussed above, the Q6 output of ripple counter 80M in Timer Control Circuit 80 will go to a logic "1" for a 1.15 second period once each 2.3 seconds while the counter is running. Each time it goes to a logic "1" FET 84B is turned on for the 1.15 second period. The circuit consisting of amplifier resistors 84C, 84E, and 84F and L.E.D. 61 is a conventional battery-level test circuit disclosed in the applications manual for the LM10H amplifier published by National Semiconductor Corporation. When FET 84B turns on it activates amplifier 84D which compares the voltages between its negative and positive inputs. If the battery charge is higher than 14 volts the amplifier will connect its No. 6 pin output terminal 84H to Ground 90. If switch 60 is closed this will close the circuit from the positive terminal 84G to ground 90 through L.E.D. 61, causing the L.E.D. to operate. If the battery voltage is below 14 volts, amplifier 84D will not connect ouput 84H to ground and L.E.D. 61 will not turn on. Thus, Battery Life-ON/OFF Indicator Circuit 84 will cause L.E.D. 61 to blink at 2.3 second intervals during the five-minute period when tne current is on, providing the battery level is above 14 volts.

There has been described a novel apparatus that greatly simplifies the administration of drugs and other chemicals by the iontophoretic method, and thereby makes the iontophoretic process a much more practical method of administration of such substances. While the invention has been described above in connection with a particular embodiment, one skilled in the art will appreciate that the invention is not necessarily so limited and that numerous other embodiments and departures from the embodiment may be made without departing from the inventive concepts. For example, many other equivalent electronic circuits may be substituted for the circuits described. Within the circuits, many substitutions and additions can be made. For example, different application times can be chosen by altering the oscillation circuit consisting of resistors 80I, 80J, 80L and capacitor 80K, or by substituting different counters for ripple counter 80M. The time may be made selectable by substituting a variable resistance for resistor 80I. Many different currents and voltages can be selected by altering the Current Control Circuit for example, the resistor 82F can be replaced by a potentiometer so that current applied can be externally varied. Other more complex timer control and current control circuits can be introduced to permit more variability in any given instrument as regards to the control of dosage and the rate and time of administration of the dosage. The electronics described have been discrete electronic components, but it is evident that equivalent microelectronic chips can be designed which would greatly reduce the size and power requirements of the element and thus permit reduction in size of the batteries leading to further reduction of size of the entire system. Likewise, housing 10 can take on many configurations and sizes. For example, the housing may be made in the form of a flexible belt of plastic or other insulative material containing the circuits in microelectronic form and the plates 20 and 21 may be in the form of metal layers painted, evaporated upon, or otherwise attached to the plastic belt. Plates 20 and 21 need not necessarily be square but may be almost any shape, and may be formed to conform to particular body contours. The plates need not be of the same size, but one plate may be substantially larger than the other. In some embodiments both plates may be relatively small compared to the housing rather than substantially covering the entire underside of the housing as in the embodiment shown. The plates need not be made of stainless steel, but may be made of other metal or any other conducting materials including flexible conducting materials. Many additional features, controls and gadgets can be added to the electronic circuitry and housing while still employing the inventive elements. Those skilled in the art will also see many other variations of the invention.

What is claimed is:

1. A device for use in iontophoretically introducing an ionic substance into body tissue, comprising:

a flexible casing of insulative material;

an electrical current source mounted within said casing;

flexible active electrode plate means located on said casing for mounting on said casing an active electrode element containing said ionic substance and for electrically coupling said electrode element to said current source; and flexible indifferent electrode means mounted on said casing for electrically coupling to said current source.

2. A device as described in claim 1 wherein said indifferent electrode means comprises an indifferent electrode plate means located on said casing for mounting on said casing an indifferent electrode element and for electrically coupling said indifferent electrode element to said electrical current source.

3. A device as described in claim 2 wherein said active electrode plate means and said indifferent electrode plate means each comprise a layer of metal on said flexible casing.

4. A device as described in claim 2 further comprising means extending between said active and said indifferent electrode plate means for preventing electrical contact between said active and indifferent electrode elements when said active and indifferent electrode elements are mounted on said active and indifferent electrode plate means respectively.

5. A device as described in claim 4 wherein said means extending between said active and indifferent electrode plate means comprises a raised portion of said casing.

6. A device for use in iontophoretically introducing an ionic substance into body tissue, comprising:

a flexible casing;

a source of electrical current, mounted within said flexible casing; and means for mounting a drug containing electrode and an indifferent electrode, comprising:

a first flexible metallic plate, mounted to said casing and coupled to said source of electrical current; and a second flexible metallic plate, mounted to said casing spaced from said first metallic plate and coupled to said source of electrical current.

* * * * *